United States Patent [19]
Guerrero et al.

[11] Patent Number: 5,762,947
[45] Date of Patent: Jun. 9, 1998

[54] COSMETIC SKIN CONDITIONING COMPOSITIONS CONTAINING A SALICYLOXY α-CARBOXY ACID

[75] Inventors: Angel Augusto Guerrero, Huntington; Joseph Michael Corey, Waterbury, both of Conn.

[73] Assignee: Elizabeth Arden Co., Division of Conopco, Inc., New York, N.Y.

[21] Appl. No.: 853,841

[22] Filed: May 9, 1997

[51] Int. Cl.$^6$ ..................................................... A61K 7/48
[52] U.S. Cl. ...................... 424/401; 514/159; 514/844; 514/937
[58] Field of Search ............................ 424/401; 514/159, 514/844, 937

[56] References Cited

U.S. PATENT DOCUMENTS

| 2,116,347 | 5/1938 | Grether et al. | 260/194 |
| 4,652,401 | 3/1987 | Schaper et al. | 252/522 R |
| 5,091,171 | 2/1992 | Yu et al. | 424/642 |
| 5,262,407 | 11/1993 | Leveque et al. | 514/159 |

FOREIGN PATENT DOCUMENTS

| 676194 | 10/1995 | European Pat. Off. . |
| 93/10755 | 6/1993 | WIPO . |

OTHER PUBLICATIONS

Derwent Abstract of JP 4036238 Published Feb. 6, 1992.

*Primary Examiner*—Jyothsan Venkat
*Attorney, Agent, or Firm*—Rimma Mitelman

[57] ABSTRACT

Cosmetic skin conditioning compositions containing a salicyloxo α-carboxy acid. The inventive compositions provide control of sebum secretion from sebocytes, improved oil control and improved skin feel, prevent shine and stickiness, while also providing anti-aging benefits which results in reduced appearance of wrinkles and aged skin, improved skin color, treatment of photoaged skin, improvement in skin's radiance and clarity and finish, and an overall healthy and youthful appearance of the skin.

5 Claims, No Drawings

COSMETIC SKIN CONDITIONING COMPOSITIONS CONTAINING A SALICYLOXY α-CARBOXY ACID

FIELD OF THE INVENTION

Cosmetic methods and compositions for conditioning human skin by topical application to the skin of cosmetic compositions containing a salicyloxy α-carboxy acid.

BACKGROUND OF THE INVENTION

Cosmetic products which improve the appearance of skin are increasingly popular with consumers. Frequently, consumers seek to alleviate or delay the signs of aged or photoaged skin, such as fine lines and wrinkles, dry and sagging skin. Consumers also frequently seek other benefits in addition to anti-aging. A frequent, undesirable skin condition is "oily skin," the condition which results from the excessive amount of sebum on the skin. Sebum is skin oil which is produced by sebocytes (cells of the sebaceous glands in the skin) and is then secreted to the skin surface. Oily skin is associated with a shiny, undesirable appearance and a disagreeable tactile sensation. Oily skin affects various age groups. Cosmetic actives which are able to provide both anti-aging benefits and sebum control are highly desirable, both from the manufacturer's and consumer's perspective.

U.S. Pat. No. 2,116,347 (Grether et al.) describes salicyloxy carboxy acid esters for external treatment of rheumatism. The Grether compounds differ from salicyloxy α-carboxy acids employed herein at least in that the '347 compounds contain an ester group in place of a terminal carboxy group. Thus, the Grether compounds contain two ester bonds, whereas the compounds included in the present invention contain only one ester bond.

PCT application WO 93/10755 reports salicylic acid as an effective anti-wrinkling agent. Leveque et al., U.S. Pat. No. 5,262,407 reports use of ring acylated salicylic acid as a treatment against skin aging. Ring alkylated salicylic acid has been reported in Japanese Patent 4036238 (Takasago Perfumery KK) for treatment of acne vulgaris. Van Scott and Yu described in a series of patents (see e.g. U.S. Pat. No. 5,091,171) anti-aging benefits of α-hydroxy acids, including removal of fine lines and wrinkles. European patent application 0676194 (Roussel Uclaf) discloses cosmetic compositions for treatment of skin aging problems, the compositions containing α-hydroxy acids (e.g. lactic acid) or esters thereof and salicylic acid or esters thereof. Salicylic acid esters disclosed in EP0676194 are non-ring esterified alkyl esters, i.e. salicylic acid is covalently bound via an ester bond to an alkyl chain.

None of the art described above discloses salicyloxy α-carboxy acids included in the present invention. Salicyloxy α-carboxy acid is, salicylic acid covalently bound via an ester bond to a group which carries an acid functionality. It has been found as part of the present invention that an α-hydroxy carboxylic acid (e.g., lactic acid) or salicylic acid when employed individually do not significantly reduce sebum secretion, whereas a salicyloxy α-carboxy acid employed in the present invention attains significant reduction in sebum secretion. Furthermore, the use of a salicyloxy α-carboxy acid is advantageous compared to using a physical mixture of salicylic acid and an α-hydroxy carboxylic acid. Salicyloxy α-carboxy acid is easier to formulate with, since an α-hydroxy carboxylic acid and salicylic acid individually carry a greater number of incompatibilities than a single molecule of a salicyloxy α-carboxy acid.

SUMMARY OF THE INVENTION

The present invention includes a skin conditioning composition comprising:

(a) from 0.0001 to 20 wt.% of a salicyloxy α-carboxy acid of Formula I:

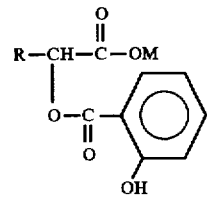

wherein R is hydrogen or an alkyl radical containing from 1 to 16 carbon atoms, and M is hydrogen or a metal cation selected from alkali or alkaline earth metals; and (b) a cosmetically acceptable vehicle.

The present invention also includes a method of controlling or preventing an oily skin condition, especially in the facial area, by applying to the skin a composition comprising a salicyloxy α-carboxy acid in a cosmetically acceptable vehicle.

The invention also includes a cosmetic method of reducing, preventing or controlling sebum secretion from sebocytes by applying the inventive composition to the skin.

The invention also includes a cosmetic method of stimulating collagen and glycosaminoglycan synthesis by fibroblasts in the skin, by applying the inventive composition to the skin.

The invention also includes a cosmetic method of treating or delaying chronoaged, photoaged, dry, lined or wrinkled skin, shielding the skin from harmful UVA and UVB light (sunscreening), increasing stratum corneum firmness and flexibility, and generally increasing the quality of skin by applying to the skin the inventive composition.

The inventive methods and compositions provide control of sebum secretion from sebocytes, improved oil control and improved skin feel, prevent shine and stickiness, while also providing anti-aging benefits which result in reduced appearance of wrinkles and aged skin, improved skin color, treatment of photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

Salicyloxy α-carboxy acids have the general Formula I:

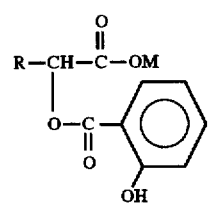

wherein R is hydrogen or an alkyl radical containing from 1 to 16 carbon atoms, and M is hydrogen or a metal cation selected from alkali or alkaline earth metals. Compounds of Formula I are collectively called "acids" herein, although salts are also included.

The preferred compounds have R=alkyl chain containing from 1 to 2 carbon atoms, and M=hydrogen, sodium, or potassium.

In the most preferred compounds, R=CH$_3$, and M=hydrogen or sodium or potassium (the compound is then also named "salicyloxy α-propionic acid").

Compounds of Formula I may be prepared by a process including the following steps:

(a) acylating a compound of Formula II

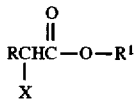

wherein X is a halogen atom and R$^1$ is any protecting group which may be removed by hydrogenation (next step in the process), with a salicylic acid salt (alkali or alkaline earth metal salt, preferably sodium, due to the commercial availability of sodium salicylate) to obtain a compound of Formula III

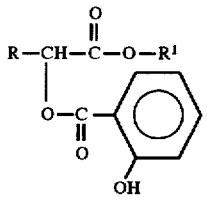

(b) hydrogenating the compound of Formula III to obtain the compound of Formula I.

The salicylic acid salt has Formula IV:

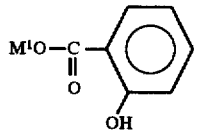

wherein M$^1$ is alkali or alkaline earth metal.

The first step of the process (step (a)) is an acylation reaction, conducted under the conditions known to one of ordinary skill. Typically, the molar ratio of compound of Formula II to the salicylate (Formula IV) is in the range of from 1:1 to 1:2, preferably the ratio is 1:1. The reaction is typically conducted in an aprotic polar solvent (such as acetone, butanone, ethyl acetate, most preferably butanone because it has a higher boiling point, hence it makes for a faster reaction). Preferably, the reaction is conducted in the presence of a catalyst (such as iodide alkaline earth salt, most preferably potassium iodide). The reaction is conducted at a temperature of 50°–100° C., most preferably at a temperature of 70°–80° C. In compound of Formula II, X is any halogen atom, preferably bromine because bromine is a better electrophile and α-bromo carboxy acids (one of the starting compounds to make Formula II) are more available commercially. R$^1$ is any protecting group which may be removed by hydrogenation and is preferably selected from the group consisting of benzyl, benzyl substituted with methoxy group, benzyloxymethyl, phenacyl, and diphenyl methane.

In the second step of the process a compound of Formula III is hydrogenated to obtain the inventive compound of Formula I. The hydrogenation conditions are familiar to one of ordinary skill in the art. Preferably the reaction is conducted at 50–200 psi, most preferably at 50–100 psi, and a temperature of 40°–80° C., preferably 50°–70° C. The reaction is conducted in the presence of Palladium, on carbon catalyst. The inventive process results in the inventive compound of Formula I. The co-products (the identity of which depends on the identity of the protecting group R$^1$) can be removed by evaporation under atmospheric or reduced pressure. The yield of the inventive compound of Formula I is typically in the range of 25 to 65 wt.%.

A compound of Formula II or may be prepared in various ways, depending on the identity of protecting group R$^1$. Thus, a compound of Formula II may be prepared by:

(i) esterifying an α-halo carboxy acid with a compound selected from the group consisting of benzyl alcohol or benzyl alcohol substituted with methoxy group to obtain a compound of Formula II wherein R$^1$ is benzyl or substituted benzyl, (ii) esterifying an α-halo carboxy acid salt with benzylchloromethyl ether to obtain a compound of Formula II wherein R$^1$ is a benzyloxymethyl;

(iii) esterifying an α-halo carboxy acid salt with phenacyl bromide to obtain a compound of Formula II wherein R$^1$ is phenacyl; and (iv) esterifying an α-halo carboxy acid with diphenyl methanol to obtain a compound of Formula II wherein R$^1$ is diphenyl methane.

The preferred compound of Formula II has R$^1$=benzyl. Thus α-halo carboxylic acid, preferably α-bromo carboxylic acid (since bromine is the best leaving group), is esterified with benzyl alcohol in the presence of dicyclohexylcarbodiimide (DCC). This reaction is preferably conducted in the inert gas atmosphere (nitrogen or argon), in a nonpolar aprotic solvent (such as halogenated solvents, hydrocarbon solvents, i.e., chloroform, methyl chloride, carbon tetrachloride, ethers, i.e. di-ethyl ether, xylene, hexane, heptane). The molar ratio of α-bromo carboxylic acid to benzyl alcohol to DCC is from 2:1:2 to 1:1:1, preferably 1:1:1. Preferably, the reaction is conducted in the presence of a catalyst (such as dimethyl-amino pyridine). The reaction is preferably conducted at a temperature of 10°–25° C., most preferably at 20°–25° C. The reaction is conducted under ambient pressure.

The salicyloxy α-carboxy acid is incorporated in the inventive compositions in an amount of from 0.0001 to 20%, preferably in order to maximize benefits at a minimum cost, in an amount of from 0.01 to 12%, most preferably from 0.1 to 8%.

Cosmetically Acceptable Vehicle

The composition according to the invention also comprises a cosmetically acceptable vehicle to act as a dilutant, dispersant or carrier for the salicyloxy α-carboxy acid in the composition, so as to facilitate its distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 mm$^2$/s (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt.% water, by weight of the vehicle. Preferably, the amount of water is at least 50 wt.% of the inventive composition, most preferably from 60 to 80 wt.%, by weight of the composition. The preferred compositions are oil-in-water emulsions, containing at least 60%, preferably at least 80% water.

Optional Skin Benefit Materials and Cosmetic Adjuncts

Although a salicyloxy α-carboxy acid has a sunscreen functionality (because it is a salicylate derivative), the inventive compositions preferably include additional sunscreens to further lower skin's exposure to harmful UV rays.

Sunscreens include those materials commonly employed to block ultraviolet light. Illustrative compounds are the derivatives of PABA, cinnamate and derivatives of salicylate (other than salicyloxy α-carboxy acid). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffinis.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Product Use, Form, and Packaging

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The cosmetic skin conditioning composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507 (silicone-based anhydrous composition within a gelatine capsule), incorporated by reference herein. The invention accordingly also provides a closed container containing a cosmetically acceptable composition as herein defined.

The following specific examples further illustrate the invention, but the invention is not limited thereto.

EXAMPLE 1

This example illustrates synthesis of salicyloxy α-propionic acid, a compound included in the inventive compositions.

Methods and Materials

Proton magnetic resonance spectra were recorded on a Bruker AC 200 model spectrophotometer. Chemical shifts are reported in parts per million from teramethylsilane as an internal standard. Spin multiplicities are indicated as follows: s (singlet), d (doublet), t (triplet), q (quartet), m (multiplet) and br (broad). The deuterated NMR solvents contain 99.0–99.8% deuterium in the indicated position, and were purchased from Cambridge Isotopic Laboratories.

Infrared spectra were recorded on a Nicolet Impact model 410 spectrometer using a NaCl cell. Data was processed using Quick IR software. Peak positions are listed in cm−1 as vs (very strong), s (strong), m (medium), w (weak) or br (broad).

Gas chromatography (GC) was performed using a Hewlett-Packard 5890 Series II gas chromatograph with an HP 7673 injector controlled by the Hewlett-Packard Chem-Station software. The Hewlett-Packard HP-1 column used was 25M×0.22 mm with a 0.33 um coating of cross-linked methyl silicone. The parameters were as follows: Inj. temp.= 250° C., initial oven temp.=50° C., initial time=5 min., rate=25° C./min., final oven temp.=250° C. Samples were analyzed as trimethyl silyl ethers/esters.

Gas chromatography/mass spectrometry was performed on a Hewlett-Packard 5890 Series II gas chromatograph in conjunction with a Finnigan MAT ITD 800 ion trap detector. The 25M×0.32 mm HP-5 column had a 0.52 um coating of 5% cross-linked phenyl methyl silicone.

Differential Scanning Calorimetry experiments were run on a Dupont DSC with a 2910 cell base and a 2100 thermal analyst. Samples of approximately 1 mg were accurately weighed into aluminum pans which were than hermetically sealed. After equilibration at 30° C., the samples were heated at a rate of 5° C./minute.

All solvents were reagent grade and were used as received. All reagents were purchased from the Aldrich or Sigma Chemical Companies and were used as received.

Step 1: Synthesis of Benzyl-2-Bromopropionate 20.0 g (0.13 moles) of 2-bromopropionic acid were stirred with 14.1 g (0.13 moles) of benzyl alcohol in dry methylene chloride at 5°–10° C., before 0.16 g (1.3e-3 moles) of 4-dimethylaminopyridine (DMAP) were added. The temperature was raised to ~15° C. before a solution of dicyclohexylcarbodiimide (DCC) (26.7 g, 0.13 moles) in dry methylene chloride was added dropwise. The solution was added at a rate as to not increase the reaction temperature above 35° C. After the imide addition was complete, the reaction proceeded at 25° C. for several hours or until infrared spectroscopy analysis indicated the absence of a carboxylic acid stretch at 1730 cm$^{-1}$. Upon completion, the reaction mixture was filtered under vacuum to remove the dicyclohexyl urea (DCU) byproduct and the filtrate was extracted once with water, once with 5% acetic acid solution (to remove DMAP) and again with water. The organic layer was dried over anhydrous magnesium sulfate before being filtered and concentrated under reduced pressure. Yield was 25 g (72%) of a mixture of Benzyl-2-bromopropionate and Benzyl-2-chloropropionate.

IR (neat): 1746 cm-1 (s)

$^{1}$H NMR (200 MHz, CdCl$_3$): d 7.3(s, 5H), 5.2(s, 2H), 4.4(qt, 1H), 1.8(d, 3H)

GC (Retention time): 11.4 minutes

Step 2: Synthesis of Benzyl Propionyl Salicylate 25 g (0.092 moles) of the above mixture were dissolved in 100 mls of 2-butanone. The precipitated dicycloxexyl urea (by-product) was filtered off and 200 mls of additional butanone were added to the filtrate. The solution was transferred to the reaction vessel before 0.15 g (9.2e$^{-4}$ moles) of potassium iodide catalyst and 14.8 g (0.092 moles) of sodium salicylate were added. The reaction solution was heated to reflux and was monitored by gas chromatography for completion. An additional one half equivalent of catalyst was necessary after several hours to drive the reaction to completion. Upon completion, the reaction mixture was cooled and filtered under vacuum to remove the sodium bromide byproduct. The butanone was removed under reduced pressure before the product was dissolved in methylene chloride and extracted once with water, once with saturated sodium bicarbonate solution and lastly with water. The organic layer was isolated and dried over anhydrous magnesium sulfate before being filtered and concentrated under reduced pressure. Yield was 26 g (82%) of 90% benzyl propionyl salicylate.

$^{1}$H NMR (200 MHz, CdCl3): d 10.4 (s, 1H), 7.9 (d, 1H), 7.4 (t, 1H), 7.3 (s, 5H), 6.9 (m, 2H), 5.4 (qt, 1H), 5.3 (s, 2H), 1.8 (d, 3H)

GC (Retention time): 16.6 minutes

DSC: Onset Temperature(°C): 164 m/z (GC/MS): 301 [M+H]$^+$

Step 3: Synthesis of Salicyloxy α-Propionic Acid 6 g (0.018 moles) of 90% Benzyl propionyl salicylate were dissolved in 400 mls of dry 2-propanol. The solution was charged into an autoclave and cooled to 10°–15° C. before being purged with nitrogen to remove air/oxygen. 1.0 g (9.0 e$^{-4}$ moles) of 10% palladium on activated carbon catalyst was then slowly added. It is important to minimize the amount of available oxygen in the vessel to prevent the ignition of 2-propanol. After addition of catalyst, the vessel was sealed and pressurized to 40–50 psi with hydrogen before being heated to 60° C. for five hours. The reaction mixture was then cooled to 20° C., filtered to remove catalyst and recharged with an additional 1.0 g of 10% palladium catalyst. The reaction was again heated to 60° C. for five hours before being cooled and filtered. The filtrate was then concentrated under reduced pressure to remove 2-propanol and the toluene byproduct. Yield was 2.6 g (65%) of 95% Salicyloxy α-Propionic Acid.

$^{1}$H NMR (200 MHz, CdCl$_3$): d 10.4 (s, 1H), 7.9 (d, 1H), 7.4 (t, 1H), 6.9 (m, 2H), 5.4 (qt, 1H), 1.8 (d, 3H)

GC (Retention time): 13.2 minutes

DSC: Onset Temperature(°C.): 133 m/z (GC/MS): 210 [M]$^+$

EXAMPLE 2

This example measures production of procollagen I by fibroblasts in response to treatment with various test compounds.

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv Derm., (1979), 73, 79–66; Smith J. et al., J. Inv. Derm., (1962), 39, pp. 347–350; and Shuster, S. et al., Br. J. Dermatol., (1975), 93, pp. 639–643); and some correlation in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with tretinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Procollagen I Staining Protocol for Slot Blot

Neonatal human dermal fibroblasts were purchased from Clonetics Corp., San Diego, Calif. All materials for cell culture were purchased from Life Technologies, NY and used in passages 5–10. Cells were seeded at a density of approximately 10,000/well in the inner 48 wells of a 96-well plate in a medium containing DMEM (Dulbecco's Modified Eagle's Medium), high-glucose supplemented with 2 ml L-glutamine, 10% fetal bovine serum, and antibiotic and antimycotic solutions. Cells were then grown to confluence for 2 days. At confluence, the medium was removed and cells were washed with serum-free DMEM, and each well dosed with 200μl of a solution of a test compound in serum-free DMEM. Each dosing was replicated in the total of six wells. Test compounds were used at concentrations indicated in Table 1 below. Control did not contain a test compound. After 24 hours, the test compound solution or the control solution was removed and cells redosed with 100µl of a solution of a test compound in serum-free DMEM. Test compounds were used at concentrations indicated in Table 1 below. After 24 hours, the test compound solution or the control solution was removed and stored over the weekend at 4° C. with protease inhibitor (Aprotinin from Sigma) in a ratio of aprotinin to water of 1:200. The test compound solution was then diluted in DMEM (approximately 20µl sample in 200µl DMEM).

Nitrocellulose membrane and 3 sheets of filter paper were soaked in TRIS buffered saline (TBS, pH 7.3.). BioRad slot blot apparatus (BioRad Labs, CA) was set up with filter paper on bottom, membrane on top, tightened. 100 ml TBS was added per well. Vacuum was used to suck wells through membrane. The test compound solution or control was vortexed, then 100µl was loaded per well and gravity dried. Procollagen from the test solution was bound to the membrane at this point in the procedure. Membrane was removed from the apparatus, excess cut off, and bottom right corner notched for orientation. The membrane was placed in blocking solution (5% milk powder in Dulbecco's phosphate buffered saline) overnight at 4° C., with shaking. The membrane was then incubated for 1.5 hrs at room temperature with 1.5 mL Rat Anti-Human Procollagen Amino-Terminal Ab (Chemicon MAB1912) in TBS with 0.1% BSA (ratio of antibody to buffer/BSA was 1:100) in a sealed bag with shaking. The membrane was then removed; washed 3 times for 5 minutes in TBS/0.1% Tween. The membrane was then incubated for 1 hour at room temperature in 2 mL of Biotinylated Anti-Rat Peroxidase-Conjugated Ab (Vector Labs) in TBS with 0.1% BSA (ratio of antibody to buffer/BSA was 1:1000) in a sealed bag with shaking.

The membrane was washed 3 times for 5 minutes in TBS/0.1%Tween. 3 mL PBS was incubated with 30µl each of solutions A and B from Vectastain Kit for 30 minutes. The membrane was placed in the resulting solution for 30 minutes in a sealed bag with shaking. The membrane was then removed and washed twice for 5 minutes in TBS/0.1%Tween. The membrane was then stained using the following solution:

12.5 mg 3-amino 9-ethyl carbazole (Sigma)
3.125 (approximately) mL DMF (N,N-dimethylformamide, from Sigma)
21.5 mL 0.2M NaOAc buffer, pH 5.2
12.5 ml $H_2O_2$ The membrane was stained until color developed and the reaction stopped with 2 washes for 10 minutes in tap water. A transparency of the blot was prepared using a color copier. The color copy was scanned using a laser densitometer (Ultroscan XL from Pharmacia KLB). Fold increase was calculated as a ratio of densitometer reading for cells treated with a test compound over control.

The results that were obtained are summarized in Table 1.

TABLE 1

| Test Compound (concentration) | Densitometer reading | Standard deviation | p-value (vs. control) | Fold increase over control |
|---|---|---|---|---|
| Experiment 1 | | | | |
| Control | 0.00209 | 0.001526 | | |
| SP (10 mM) | 0.002587 | 0.001642 | 0.696535 | 1.2 |
| SP (2 mM) | 0.00434 | 0.001521 | 0.081808 | 2.1 |

TABLE 1-continued

| Test Compound (concentration) | Densitometer reading | Standard deviation | p-value (vs. control) | Fold increase over control |
|---|---|---|---|---|
| Experiment 2 | | | | |
| Control | 0.002387 | 0.000926 | | |
| SP (5 mM) | 0.00388 | 0.000306 | 0.027063 | 1.6 |
| SP (1 mM) | 0.00549 | 0.001875 | 0.048601 | 2.3 |

SP = salicyloxy α-propionic acid

Salicylic acid and lactic acid, each increased procollagen I production by fibroblasts (data not shown).

It can be seen from the data in Table 1 that the addition of salicyloxy α-propionic acid at 1, 2 and 5 mM concentrations to fibroblast cultures resulted in increased procollagen I production, as indicated by higher densitometer readings compared to control. It is believed that salicyloxy α-propionic acid at concentrations of 10 mM damaged the fibroblast cultures.

EXAMPLE 3

This example measures production of glycosaminoglycans by fibroblasts in response to treatment with various test compounds. Glycosaminoglycans (GAGs) are a family of polysaccharides which (with the exception of hyaluronic acid (HA)) can be linked to a protein core, forming a proteoglycan. The main GAGs in the dermis are HA and dermatan sulfate, with chondroitin-4-sulfate and chondroitin-6-sulfate present in small amounts. Made by both keratinocytes and dermal fibroblasts, GAGs are essential components of the extracellular matrix, although they make up only 0.20% of the dry weight of skin. GAGs hydrate in the skin (HA can hold up to 1000× its mass in water) and maintain basement membrane integrity, regulate cellular interactions and nutrient transport, and are involved in collagen and possibly elastic fiber formation. The proportion of GAGs (especially HA) in the dermis has been shown to be diminished with aging. See Perlish et al, "The Role of Glycosaminoglycans in Aging of the Skin." Retinoic acid, the benchmark anti-aging active, has been shown to increase GAG content of the spinous and granular layers of the epidermis and the papillary dermis of aged skin in vivo. See Kligman et al., "Effects of topical tretinoin on non-sun-exposed protected skin of the elderly." J. Am Acad Dermatol 1993;29:25–33.

Protocol for measuring GAGs

Neonatal human dermal fibroblasts were purchased from Clonetics Corp., San Diego, Calif. All materials for cell culture were purchased from Life Technologies, NY and used in passages 5–10. Cells were seeded at a density of approximately 10,000/well in the inner 48 wells of a 96-well plate in a medium containing DMEM (Dulbecco's Modified Eagle's Medium), high-glucose supplemented with 2 mM L-glutamine, 10% fetal bovine serum, and antibiotic and antimycotic solutions. Cells were then grown to confluence for 2 days. At confluence, each well was rinsed in serum-free DMEM and the cells dosed with test compounds (in triplicate) in 750µl of serum-free DMEM. Test compounds were used at a concentration indicated in Table 2 below. Controls did not contain any test compounds. After 24 hours, this medium was aspirated and the treatment step repeated. After a second 24-hour period, this medium, containing the soluble GAGs, was collected and frozen until analysis.

A positively-charged Zeta Probe membrane was soaked in sterile water and placed into the Dot-Blot Apparatus (both Bio-Rad Labs, Hercules, Calif.). 100µL of water was applied to each well and pulled through using a vacuum. After thawing, 100µL of test solution samples or standards (Hyaluronic acid or Chondroitin Sulfate from bovine trachea, Sigma, St. Louis, Mo.) was applied to the membrane and allowed to gravity filter (about 1.5–2 hours). GAGs were now bound to membrane. The membrane was blocked in 3% w/v fatty acid free bovine serum albumin (Sigma) in water for one hour. A dye solution of 0.5% w/v Alcian Blue dye (ICN Biochemicals, Cleveland, Ohio) in 3% acetic acid, pH approximately 2.3, was made. The membrane was washed twice in distilled water and then stained in the dye solution on a rotary shaker for 15 minutes. The dye was poured off and the membrane destained twice for 15 minutes each time in 3% acetic acid. The membrane was rinsed in water and left to dry overnight. The Bio-Rad Image Analysis Densitometer was used to quantitate the intensity of color in each spot. Fold increase over control was calculated as a ratio of densitometer reading for cells treated with a test compound over control.

The results that were obtained are summarized in Table 2.

TABLE 2

| Test Compound (concentration) | Densitometer reading | Standard Deviation | p-value (vs. control) | Fold increase over control |
|---|---|---|---|---|
| Experiment 1 | | | | |
| Control | 0.36325 | 0.025158 | | |
| SP (5 mM) | 0.38875 | 0.036582 | 0.294402 | 1.1 |
| SP (1 mM) | 0.41925 | 0.05818 | 0.127663 | 1.2 |
| Experiment 2 | | | | |
| Control | 0.357 | 0.039556 | | |
| SP (5 mM) | 0.403 | 0.017795 | 0.078168 | 1.1 |
| SP (1 mM) | 0.49125 | 0.034189 | 0.002146 | 1.4 |

SP = salicyloxy —propionic acid

Lactic acid increased GAGs production, but salicylic acid did not (data not shown).

It can be seen from the data in Table 2 that the addition of salicyloxy α-propionic acid at 1 mM concentration to fibroblast cultures resulted in increased GAGs production, as indicated by higher densitometer readings compared to control. Maximum fold increase over control observed in this assay, using transforming growth factor β, was about 2.

EXAMPLE 4

This example reports an in vitro analysis of sebum suppression by various test compounds.

In Vitro Sebocyte Lipogenesis Assay

Human sebaceous glands were isolated from the nose of a male (age 60) and cultured using submerged tissue culture techniques (Bajor et al, J. Invest. Dermatol. 102: 1994, P. 564). These sebocytes accumulate intracellular lipid droplets characteristic of mature human sebum. Lactic and salicylic acids were obtained from Sigma.

Harvested and passaged sebocytes were added to each well of a 48 well tissue culture plate and incubated at 37° C. in the presence of 7.5% $CO_2$ for 10 days. On the day of experimentation, the growth medium was removed and the sebocytes washed three times with phosphate buffered saline (PBS). Fresh PBS in 0.5 ml amount was added to each well and 5 ml of a test agent, at final concentrations ranging from 0.001% to 0.2%. Triplicate wells were utilized for each sample. Controls consisted of PBS, dimethyl sulfoxide (DMSO) used to solubilize the salicyloxy α-propionic acid, and phenol red, a compound which possesses estrogen-like activity (Phenol Red decreases sebum production and was used as a control to verify the integrity of the sebocyte assay). All cultures were incubated at 37° C./7.5% $CO_2$ for 30 minutes. Radioactive label was prepared by adding 100 ml of $^{14}C$ labeled acetic acid (Amersham, sodium salt, specific activity of 56 mCi/mmol) to 10 ml of 50 mM sodium acetate buffer. Then, 50 ml was added to each well containing the sebocytes and test agents. The cultures were returned to the incubator for four hour. Thereafter, the sebocytes were rinsed three times with fresh PBS to remove unbound active and radioactive label. Radioactive label remaining in the cultured sebocytes was counted using a Beckman scintillation counter. The results were expressed as % reduction compared to control (DMSO).

The results that were obtained are summarized in Table 3 below.

TABLE 3

| Compound | % Final Concentration | % Reduction in $^{14}C$ Label Incorporation | Standard Deviation |
|---|---|---|---|
| Experiment 1 | | | |
| SP | 0.001 | 3.9 | 31.4 |
| | 0.01 | 18.7 | 4.5 |
| | 0.10 | 67.8 | 5.3 |
| | 0.20 | 68.9 | 3.6 |
| Experiment 2 | | | |
| SP | 0.001 | 24.4 | 5.6 |
| | 0.01 | 53.3 | 3.8 |
| | 0.10 | 91.6 | 1.2 |
| | 0.20 | 87.1 | 5.0 |
| Phenol Red | 0.01 | 20.5 | 22.5 |
| Experiment 3 | | | |
| SP | 0.001 | −57.0 | 4.7 |
| | 0.005 | −49.3 | 7.7 |
| | 0.10 | 75.8 | 17.4 |
| Experiment 4 | | | |
| SP | 0.01 | 2.4 | 14.8 |
| | 0.05 | 22.6 | 9.1 |
| | 0.10 | 73.8 | 11.7 |
| Experiment 5 | | | |
| Lactic Acid | 0.001 | 5.9 | 20.1 |
| | 0.01 | 3.0 | 10.9 |
| | 0.1 | 38.6 | 5.0 |
| | 1.0 | 15.1 | 1.9 |
| Experiment 6 | | | |
| Salicylic Acid | 0.0014 | 10.1 | 10.5 |
| | 0.014 | 13.1 | 13.4 |
| | 0.14 | 3.6 | 7.4 |

SP = salicyloxy α-propionic acid

It can be seen from the results in Table 3 that at a concentration of 0.10% and higher salicyloxy α-propionic acid consistently suppressed sebum secretion by sebocytes. In three out of four experiments, salicyloxy α-propionic acid was effective even at a concentration lower than 0.01%. Lactic acid was substantially less effective at 0.1% than salicyloxy α-propionic acid at the same concentration. Salicylic acid was not effective.

EXAMPLE 5

Example 5 illustrates topical compositions according to the present invention. The compositions can be processed in conventional manner. They are suitable for cosmetic use. In particular the compositions are suitable for application to wrinkled, rough, flaky, aged and/or UV-damaged skin and/or oily skin to improve the appearance and the feel thereof as well as for application to healthy skin to prevent or retard deterioration thereof.

OIL-IN-WATER EMULSION

| INGREDIENT | % w/w |
|---|---|
| DI Water | 73.40 |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| Salicyloxy α-propionic acid | 8.00 |
| Isopropyl Myristate | 5.00 |
| Octyl Palmitate | 3.00 |
| Cetyl Alcohol | 1.00 |
| Dimethicone, 100 cst | 0.50 |
| Beeswax | 0.30 |
| Propylparaben | 0.10 |
| Germall II | 0.10 |
| Fragrance | 0.10 |
| Total -> | 100.00 |

OIL-IN-WATER EMULSION

| INGREDIENT | % w/w |
|---|---|
| DI Water | 71.20 |
| Xanthan Gum | 0.20 |
| Disodium EDTA | 0.10 |
| Glycerin | 5.00 |
| Butylene Glycol | 2.00 |
| Methylparaben | 0.30 |
| Salicyloxy α-hexadecanoic acid | 8.00 |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-21 | 3.00 |
| Propylparaben | 0.10 |
| Germall II | 0.10 |
| Fragrance | 0.10 |
| Total -> | 100.00 |

WATER-IN-OIL EMULSION

| INGREDIENT | % w/w |
|---|---|
| DI Water | 63.30 |
| Disodium EDTA | 0.10 |
| Glycerin | 3.00 |
| Propylene Glycol | 2.00 |
| Sodium Chloride | 0.70 |
| Methylparaben | 0.30 |
| Cyclomethicone | 14.00 |
| Salicyloxy α-pentanoic acid | 5.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |

-continued
WATER-IN-OIL EMULSION

| INGREDIENT | % w/w |
|---|---|
| Germall II | 0.10 |
| Fragrance | 0.10 |
| Total -> | 100.00 |

HYDRO-GEL

| INGREDIENT | % w/w |
|---|---|
| DI Water | 82.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Salicyloxy α-heptanoic acid | 1.00 |
| Methylparaben | 0.30 |
| Polysorbate 20 | 0.25 |
| Disodium EDTA | 0.10 |
| Germall II | 0.10 |
| Total -> | 100.00 |

ANHYDROUS SERUM

| INGREDIENT | % w/w |
|---|---|
| Cyclomethicone | 72.40 |
| Salicyloxy α-propionic acid | 5.00 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| Total -> | 100.00 |

HYDRO-ALCOHOLIC GEL

| INGREDIENT | % w/w |
|---|---|
| DI Water | 52.55 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Salicyloxy α-dodecanoic acid | 1.00 |
| Methylparaben | 0.30 |
| Polysorbate 20 | 0.25 |
| Disodium EDTA | 0.10 |
| Germall II | 0.10 |
| Total -> | 100.00 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin conditioning composition comprising:
   (a) from 0.0001 to 20 wt.% of a salicyloxy α-carboxy acid of Formula I:

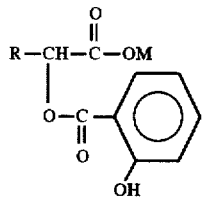

wherein R is hydrogen or an alkyl radical having from 1 to 16 carbon atoms, and M is hydrogen or a metal cation selected from alkali or alkaline earth metals; and
   (b) a cosmetically acceptable vehicle.

2. The composition of claim 1 wherein R is $CH_3$.

3. The composition of claim 2 wherein M is hydrogen or sodium.

4. A method of controlling an oily skin the method comprising applying to the skin, the composition according to claim 1.

5. A method of reducing or controlling sebum secretion from sebocytes in the skin, the method comprising applying to the skin the composition according to claim 1.

* * * * *